US010775328B2

(12) United States Patent
Dioszegi et al.

(10) Patent No.: US 10,775,328 B2
(45) Date of Patent: Sep. 15, 2020

(54) METHOD OF AND DEVICE FOR ANALYSING A PHASE TRANSFORMATION OF A MATERIAL

(71) Applicant: Tekniska Högskolan i Jönköping Aktiebolag, Jönköping (SE)

(72) Inventors: Attila Dioszegi, Jönköping (SE); Péter Svidro, Jönköping (SE)

(73) Assignee: Tekniska Högskolan i Jönköping Aktiebolag, Jönköping (SE)

( * ) Notice: Subject to any disclaimer, the term of this patent is extended or adjusted under 35 U.S.C. 154(b) by 248 days.

(21) Appl. No.: 15/763,636

(22) PCT Filed: Sep. 8, 2016

(86) PCT No.: PCT/EP2016/071146
§ 371 (c)(1),
(2) Date: Mar. 27, 2018

(87) PCT Pub. No.: WO2017/055046
PCT Pub. Date: Apr. 6, 2017

(65) Prior Publication Data
US 2018/0284043 A1 Oct. 4, 2018

(30) Foreign Application Priority Data

Sep. 29, 2015 (SE) ...................................... 1551243

(51) Int. Cl.
*G01N 25/02* (2006.01)
*G01K 7/00* (2006.01)
(Continued)

(52) U.S. Cl.
CPC ................ *G01N 25/04* (2013.01); *B01L 3/04* (2013.01); *G01K 13/125* (2013.01); *G01N 1/125* (2013.01);
(Continued)

(58) Field of Classification Search
USPC .......................... 374/16, 143, 166, 110, 208
See application file for complete search history.

(56) References Cited

U.S. PATENT DOCUMENTS

2005/0008063 A1* 1/2005 Chippett ................ G01K 17/00
374/34

FOREIGN PATENT DOCUMENTS

| DE | 8707781 U1 | 7/1987 |
| EP | 1925936 A1 | 5/2008 |
| WO | 9944022 A1 | 9/1999 |

OTHER PUBLICATIONS

International Search Report and Written Opinion issued in counterpart PCT Application No. PCT/US2016/071146 dated Nov. 15, 2016.

* cited by examiner

*Primary Examiner* — Mirellys Jagan
(74) *Attorney, Agent, or Firm* — Olive Law Group, PLLC

(57) ABSTRACT

A method of analyzing a phase transformation process of a material comprises providing a spherical sample of the material, measuring and recording a first data series of core temperature at the sample's center of gravity, measuring and recording a respective second data series of temperature at the sample's periphery, measuring and recording a respective third data series of radial displacements at the sample's periphery, and calculating a change in pressure in the sample at a plurality of points in time based on first, second and third said data series.

15 Claims, 5 Drawing Sheets

(51) Int. Cl.
*G01K 1/00* (2006.01)
*G01K 3/00* (2006.01)
*G01N 25/04* (2006.01)
*G01N 33/205* (2019.01)
*B01L 3/04* (2006.01)
*G01N 1/12* (2006.01)
*G01K 13/12* (2006.01)
*B22D 2/00* (2006.01)

(52) U.S. Cl.
CPC ...... *G01N 33/205* (2019.01); *B01L 2200/147* (2013.01); *B01L 2300/04* (2013.01); *B22D 2/006* (2013.01)

METHOD OF AND DEVICE FOR ANALYSING A PHASE TRANSFORMATION OF A MATERIAL

CROSS REFERENCE TO RELATED APPLICATIONS

This is a 371 national stage patent application, which claims priority to PCT International Patent Application No. PCT/EP2016/071146, filed Sep. 8, 2016, and titled METHOD OF AND DEVICE FOR ANALYSING A PHASE TRANSFORMATION OF A MATERIAL, which claims the benefit of Sweden Patent Application Number 1551243-7, filed Sep. 29, 2015, the disclosures of which are incorporated herein by reference in their entireties.

TECHNICAL FIELD

The present disclosure relates to a method of analyzing a phase transformation process of a material. The disclosure also relates to a device for carrying out the method.

The method is particularly suited for analyzing a phase transformation of a metal or metal alloy, and especially the solidification of a metal or metal alloy melt.

BACKGROUND

In connection with casting of metals, there is a risk of defect formation occurring during the solidification process, i.e. when the liquid metal solidifies. When such defects occur, the entire product may need to be scrapped and typically re-melted. In worst case, the defect is not discovered until later, e.g. when the product fails, whereby product safety is compromised.

Some defects are related to the composition of the melt and can, in some cases and within some limits, be compensated for by providing additives to the melt Hence, there is a need for predicting the behavior of the melt during the solidification process.

EP1032718B1 discloses a method of producing a compacted graphite iron casting or spheroidal graphite cast iron, wherein a sampling operation is performed for determining an amount of structure-modifying agent that is to be added to the melt in order to obtain the desired type of iron.

EP0805964B1 discloses a sample holder that may be used in the method of EP1032718B1.

There is still a need for improvements in the prediction of phase transformations, such as solidification processes.

SUMMARY

An object of the present disclosure is to provide an improved method for prediction of phase transformation processes, including solidification processes of a metal melt, and a sampling device which can be used in the method. A specific object is to provide increased reliability in predicting defects.

The invention is defined by the appended independent claims with embodiments being set forth in the dependent claims, in the following description and in the drawings.

According to a first aspect, there is provided a method of analyzing a phase transformation of a material. The method comprises providing a spherical sample of the material, measuring and recording a first data series of core temperature at the sample's center of gravity, measuring and recording a respective second data series of temperature at the sample's periphery, measuring and recording a respective third data series of radial displacements at the sample's periphery, and calculating a change in pressure in the sample at a plurality of points in time based on first, second and third said data series.

The invention is based on the understanding that it is possible to calculate pressure changes in a material, which occur during a phase transformation process. Based on knowledge of such pressure changes, it is possible to make conclusions relating to the risk of defects occurring during the solidification process. For example, shrinkage defects can be associated with underpressure during parts of the solidification process.

A preferred sampling holder may be one comprising a spherical container as described below.

The method may further comprise presenting the calculated change in pressure on a user interface. Such a user interface may be a computer screen or a printout.

In the method, the peripheral temperature may be measured in at least two spaced apart points on the periphery of the sample, and the displacements may be measured in at least two spaced apart points on the periphery of the sample, said at least two points define a three dimensional geometric body.

By measuring in more than one point, it is possible to obtain data on orientation of the thermal field.

At least one of the peripheral temperatures may be measured in a point where also displacement is measured.

At least one of the temperature at the sample's periphery and the radial displacements at the sample's periphery may be measured in at least four points, which define a three dimensional geometric body.

The four points where the temperature and/or the four points where the displacements are measured may define a tetrahedron, preferably a regular tetrahedron.

In the method, the measuring steps may be performed until the material has reached an end of the phase transformation process.

The method may further comprise reducing noise in at least one of the data series.

Such noise reduction may be performed by e.g. calculating a moving average or by applying an interpolation algorithm.

The method as claimed in any one of the preceding claims, further comprising calculating an average surface temperature and/or radial displacement over said at least two points for one or more points in time.

The method may further comprise calculating release of latent heat ($q_s(t)$) at a plurality of points in time, during at least a solidification time interval, based on the first, second and third data series.

The latent heat may be calculated for each point in time using Fourier thermal analysis based on numerical solution of the heat conduction equation. The outcome will be the release of latent heat as a function of temperature.

Calculating the change of pressure in the material at a plurality of points in time may be based on the release of latent heat (qs(t)), the temperature and a volume change, for the respective point in time.

Calculation of the pressure may be achieved by using the Clapeyron equation, wherein pressure is calculated as a function of the local temperature, released latent heat and the volume change of the sample within the solidification interval. The outcome will be the change of pressure as a function of temperature.

DETAILED DESCRIPTION

The description will be directed to a phase transformation process in the form of a solidification process of a liquid metal melt transforming to solid phase.

The description will initially be directed to a sampling holder for collecting and holding an amount of the metal melt that is to be tested.

Figure 1:
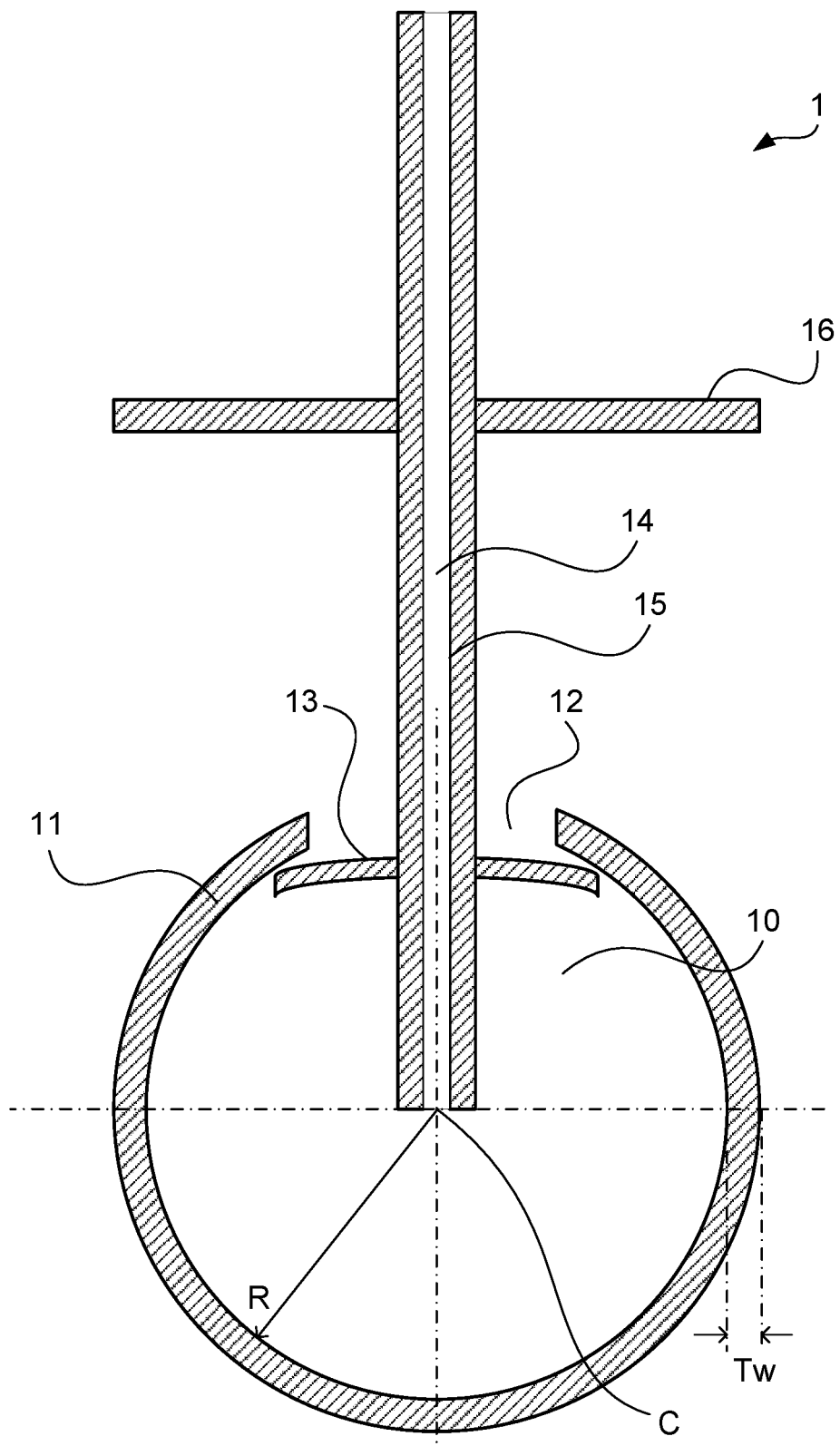
FIG. 1 is a schematic sectional view of a sample holder.

Referring to FIG. 1, there is illustrated a sample holder 1 comprising a hollow receptacle 10, 11, which presents a substantially spherical shape. The receptacle comprises a receptacle space 10, which is enclosed by a receptacle wall 11.

The receptacle may be spherical in that a radius R from a center C of the receptacle is the same for any direction inside the space 10. However, such a receptacle may be difficult to produce, and in reality, minor deviations must be accepted. For example, the radius may vary less than 10%, preferably less than 1% or less than 0.5% between a maximum radius and a minimum radius.

The receptacle wall 11 may be formed of a thin plate of a material having a higher melting point than the material that is to be sampled.

The wall thickness Tw should be as small as possible. Where the receptacle is formed of a material that has a melting point that is close to that of the melt to be sampled, wall thickness Tw may be adapted to allow for a sufficient exposure time without collapsing.

For example, the concept of additives which modify melting point is well known to the skilled person.

Typical wall thicknesses may be less than 3 mm, less than 2 mm, less than 1.5 mm, less than 1 mm, less than 0.75 mm or less than 0.5 mm.

For example, a sample holder for sampling an iron melt may be formed of a steel plate having higher carbon content than the iron melt.

The receptacle may be formed by forging plate blanks into respective part-spherically shaped pieces and then assembling the pieces by e.g brazing, welding or soldering to form a hollow body having a sufficiently thin wall.

Plate blanks may be forged or pressed into hemispheres or spherical lunes, which may be joined as mentioned above.

At joints thus formed, additional tolerance for variation in the radius R may need to be tolerated.

As further options, the receptacle may be formed by casting or molding.

As yet another option, the receptacle may be formed by metal spinning using a meltable or incinerable core of e.g. wax, polymer, or even ice, whereby a plate blank is shaped into a one piece spherical hollow body, after which the core is removed.

An inside and/or outside of the receptacle may be surface treated to enhance or reduce adhesion of the melt that is to be sampled, or in order to protect the sample holder from premature degradation on contact with the melt. For example, such surface treatment may be provided in order to protect the receptacle surface from thermal shock, as would be the case with a graphite based surface coating.

The receptacle 10 may have a single opening 12 through which the melt to be sampled may be let in and through which air may escape during such process.

A cover member, such as a lid 13 may be provided to cover the opening, prevent splashing and reduce heat flux at the opening 12, in order to keep the heat flux as even as possible over the receptacle surface.

The cover member may be provided as a lid as illustrated in FIG. 1. Such a lid 13 may be positioned on an inside of the receptacle and be given a shape of a segment of a sphere having a major diameter that is slightly greater than a major diameter of the opening 12. Hence, the size of the lid 13 may prevent it from leaving the receptacle through the opening 12.

In alternative embodiments, the lid could be attached to the receptacle by a hinge mechanism.

In the illustrated embodiment, a tube 15 extends to the center C of the receptacle space 10.

The tube 15 may have an inner channel 14, which with a sufficient diameter for it to receive a temperature sensor and associated connection, such as wiring, for connecting the sensor to a measuring device.

The tube 15 may extend into the space 10 to such an extent that a temperature sensor (not shown), when received in the channel 14, is positioned so as to provide a temperature reading at the center C of the receptacle.

For example, the tube 15 may extend to the center C of the receptacle, as illustrated in FIG. 1.

In the example illustrated in FIG. 1, the tube 15 extends through the lid 13 and may be fixedly connected to the lid.

Hence, in an embodiment where the lid 13 is prevented from leaving the space 10, also the tube 15 may be prevented coming loose from the receptacle.

Moreover, the tube 15 may extend outside of the receptacle such that it can be gripped and used for example for holding the sample holder 1 when collecting the sample and/or when performing measurements on a collected sample.

The tube 15 may be provided with a splash protection 16, which may prevent such splashing as may occur when air escapes out of the receptacle through the opening 12 when the sample holder is submerged into a metal melt. The splash protection may be provided in the form of a substantially flat disc.

In alternative embodiments, the tube 15 may extend through a wall 11 of the receptacle. Thus in such embodiments, a through hole through which the tube 15 extends into the space 10 may be spaced from the opening 12.

Also, in such an embodiment the lid may be separate from the tube 15, as mentioned above.

In further alternatives, the lid may be dispensed with, e.g. provided the additional heat flux can be dealt with or ignored.

An embodiment would also be conceivable where a skeleton lid is provided, i.e. a lid which connects with the tube and prevents the tube from leaving the receptacle, but which has holes or openings that allow additional heat flux.

The receptacle wall 11, the lid 13, the tube 15 and the splash protection 16 may be made of the same material.

Referring to FIGS. 2a-2d, a sampling method will now be described, in which a sample holder 1 as described above may be used.

It is recognized that the sample collection may be performed by hand by simply lowering the sample holder receptacle into the melt until it has filled with molten metal and then withdrawing it and placing it in a measurement fixture.

In the following, it is envisaged that an automated sample collection device may be desirable. Such a device may comprise a holder gripping device 31, a tilt joint 32 (which is optional), a holder cradle 33 and a guide rail 34, along which the cradle 33 may travel. The guide rail may be provided 34 with a first actuator (not shown) for causing the cradle 33 to travel along the guide rail 34 in a controlled manner. Moreover, the cradle 33 and/or the tilt joint 32 may comprise a second actuator (not shown) for causing the gripping device 31 to tilt relative to the cradle 33.

Figure 2A:
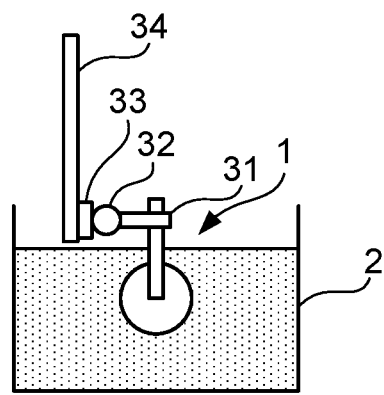
FIGS. 2a-2d schematically illustrate steps of a sample collection and measurement method.
Figure 2B:
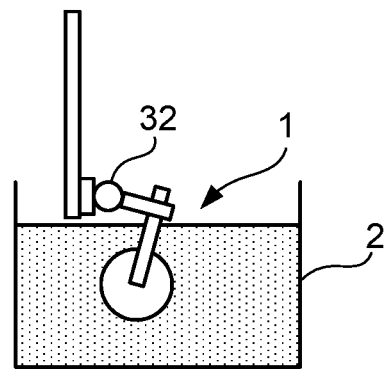
Figure 2C:
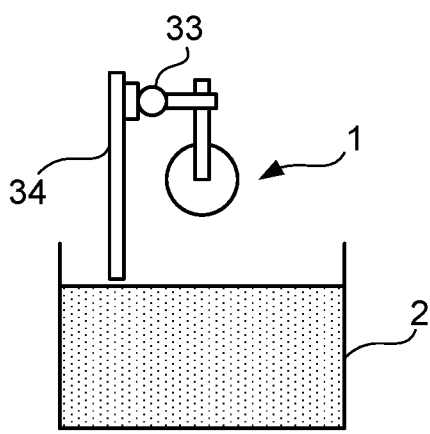
Figure 2D:
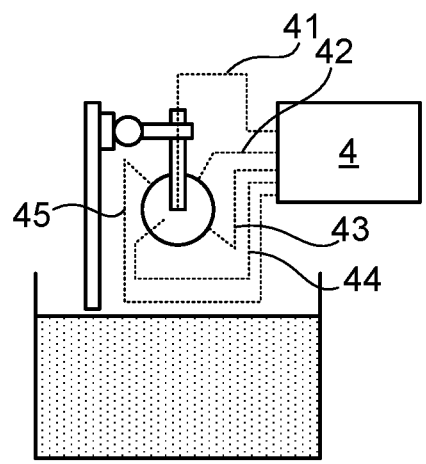
Figure 3:
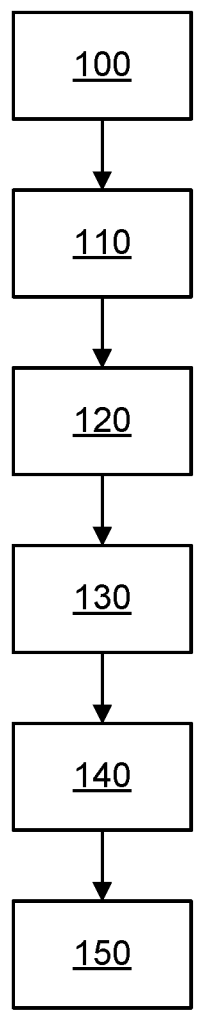
FIG. 3 is a schematic flow chart of a method of analyzing a solidification process.

Referring to FIG. 2d, a measurement device 4 may be provided. The measurement device may be based on a programmable computer having an interface for connecting to a plurality of measurement probes 41, 42, 43, 44, 45.

The measurement device may also comprise a controller that is arranged to provide signals for controlling the movements of the cradle 33 and/or the tilt joint 32.

A sample collecting operation, wherein a sample of liquid metal is collected from a vessel 2 may be performed as follows.

Referring to FIG. 2a, a sample holder 1 is positioned to be held by the gripping device 31. In the illustrated example, the tube 15, e.g. a free end thereof, may be grasped by the gripping device 31.

The gripping device 31 may be heat insulated so as to counteract heat transfer from the holder 1. For example, the gripping device may be formed of a material having very low heat conductivity, and the part of the gripping device engaging the holder 1 may be made as small as possible.

At this stage, a temperature probe 41 may be inserted into the channel 14 of the tube such that a sensing element is arranged at the center C of the space 10.

The cradle 33 is displaced along the guide 34 such that the receptacle is submerged into the melt. Through the buoyancy of the initially air-filled receptacle, the tube 15 and the lid which is attached thereto will shift downwardly relative to the opening 12, such that the liquid metal may flow into the space 10 through the opening 12.

Referring to FIG. 2b, the sample holder 1 may be tilted by about 5°-30° in order to ensure that no air is trapped under the lid and the space 10 is completely filled with liquid metal.

Referring to FIG. 2c, the sample holder 1 may be withdrawn and lifted from the liquid metal by the cradle 33 being displaced along the guide rail 34 to a measuring position. Before, during or after the withdrawal of the sample holder, any tilting may be reset such that the tube 15 is centered in the opening 12 and the lid 13 completely covers the opening 12.

Referring to FIG. 2d, at the measuring position, temperature and radial displacement will be measured and recorded at different spots on the receptacle wall 11 during a solidification period. Such measurement may commence immediately on the sample holder reaching the measuring position.

In one embodiment, four measurement spots may be provided with temperature and radial displacement being measured at each spot.

In an alternative embodiment, four temperature measurement spots and four radial displacement measurement spots are provided, each of which being spaced from a respective temperature measurement spot. Such displacement may be kept to a minimum, such as less than 1 cm, less than 0.5 cm or less than 0.25 cm.

Also during the solidification period, temperature is measured and recorded at the center C of the space 10.

The temperatures and displacements may be recorded with a sampling rate of 0.5-20 Hz, preferably 5-10 Hz.

The measurement, and thus the recording, may continue until the sample has reached a predetermined degree of solidification. If the measurement starts with a sample having only liquid phase, this predetermined degree of solidification may be where the solidification process has ended. The measurement may continue until a predetermined temperature is reached, or through a predetermined time period after such temperature has been reached. The time period that is analyzed may constitute a subset of the total measuring time.

It is possible to protect the measurement position from e.g. draft, by introducing surrounding walls, which may be thermally insulated, but this is not necessary.

The description will now focus on the method of analyzing a sample taken using the sampling device. An overview of the nomenclature used in the equations is provided at the end of the present description.

In a first step 100, the sampling device containing melt is introduced into the measuring position and measurements of core temperature, four different surface temperatures and four different radial displacements are provided.

Hence, each input data point may contain time, core temperature, first surface temperature, second surface temperature, third surface temperature, fourth surface temperature, first radial displacement, second radial displacement, third radial displacement and fourth radial displacement.

In a second step 110, a noise reduction algorithm may be applied to the measured data. Such a noise reduction algorithm may comprise a moving average or an interpolation algorithm. For example, for each point an average may be calculated based on the value in the point and in its neighboring points.

Hence, each noise reduced data point may contain time, noise reduced core temperature, noise reduced first surface temperature, noise reduced second surface temperature, noise reduced third surface temperature, noise reduced fourth surface temperature, noise reduced first radial displacement, noise reduced second radial displacement, noise reduced third radial displacement and noise reduced fourth radial displacement.

In a third step 120, the surface temperatures $T_2$ may be averaged.

In a basic embodiment, an average may be calculated based on the four temperatures measured at the surface at each point in time.

In a another embodiment, a temperature gradient may be provided based on the four points measured at each point in time, whereupon a difference in temperature between an actual temperature and a predicted temperature at one or more of the points may indicate that the receptacle is not entirely spherical and/or that the sensing element arranged at the center C of the receptacle is in fact not exactly centered.

Based on this measurement, it is possible to determine and compensate for the displacement of the wall from the theoretical centre point.

Figure 4:
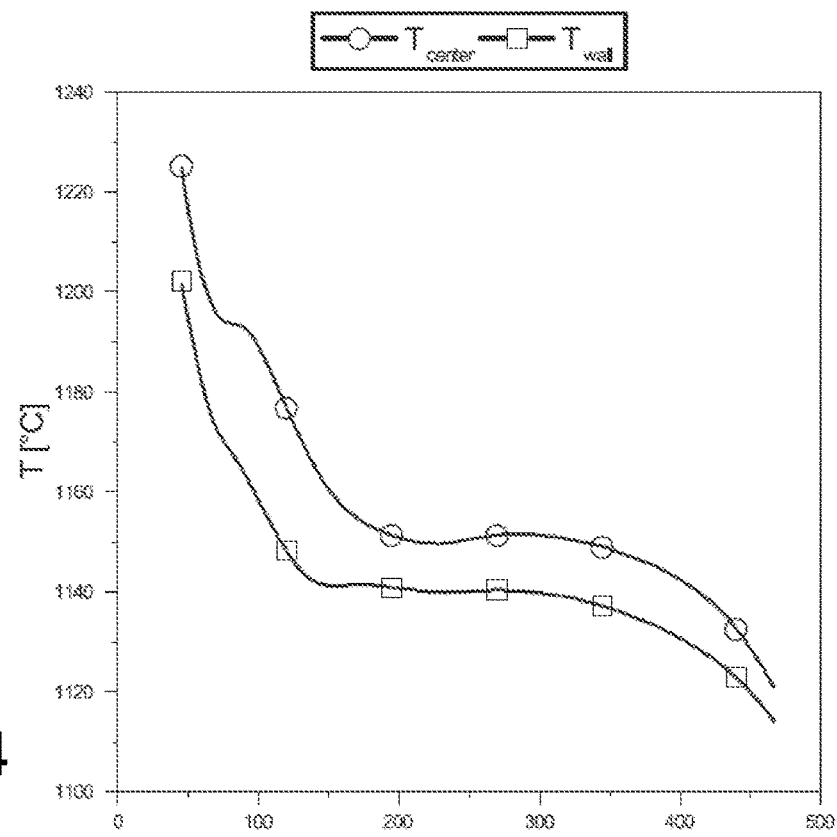
FIG. 4 shows recorded and smoothed cooling curves in the central thermocouple ($T_C$) and the average outer temperature on the surface of the sample ($T_W$).

Based on an experimental measurement, an example of average core temperature T1 and average (according to the basic embodiment) peripheral temperature T2 is plotted in FIG. 4.

In the experiment, a ferrous material having the following composition (with the remainder being Fe) was used:

| | Element | | | | | | |
|---|---|---|---|---|---|---|---|
| | C | Si | Mn | P | S | Cr | Mo | Cu |
| % by weight | 3.5 | 1.8 | 0.6 | 0.05 | 0.1 | 0.15 | 0.25 | 0.88 |

The material was melted in a 50-kg medium frequency induction furnace. The material was superheated to 1460° C. and held for 20 minutes. The material was provided with a strontium based inoculant where the added inoculant was 0.05% by weight of the total melt. The inoculant was added in the stream while the metal was trapped to a two hand ladle at a temperature of 1440° C.

In a fourth step 130, the radial displacements are averaged.

In the basic embodiment, an average radial displacement may be calculated for each point in time.

Hence, in the basic embodiment, each data point may contain time, core temperature $T_1$, average peripheral temperature $T_2$ and average displacement $R_2$.

In a fifth step 140, volume change of the sampling device is calculated based on the average displacement $R_2$.

Figure 5:
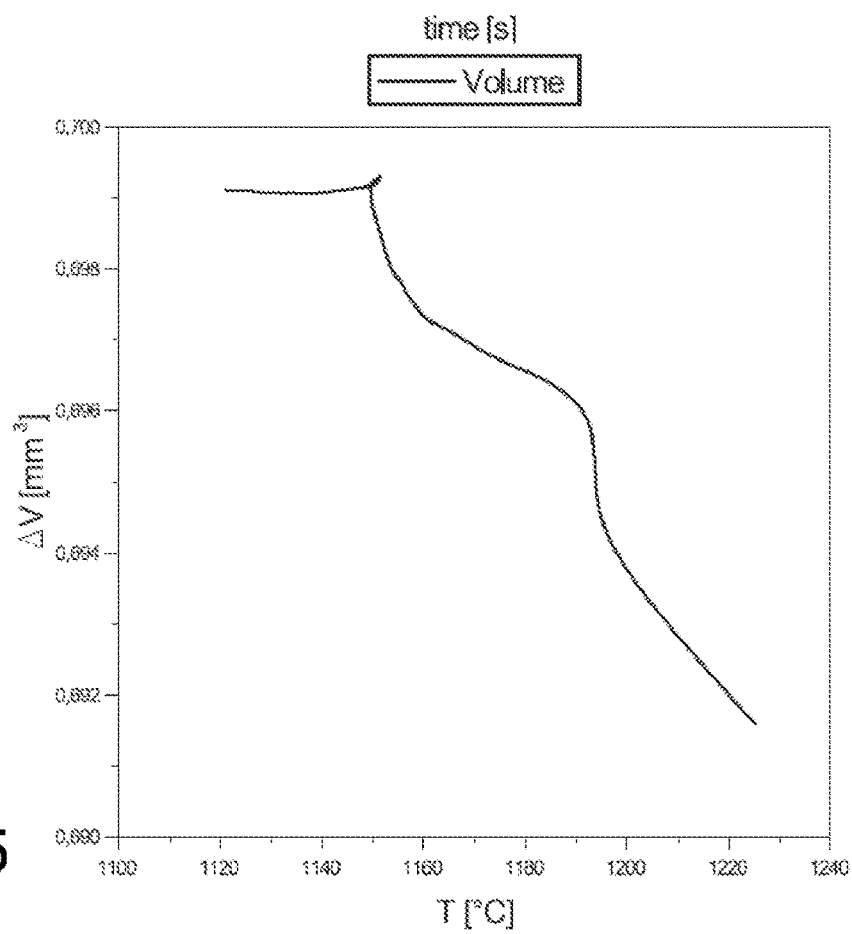
FIG. 5 shows calculated volume change based on the measured diameter of the spherical sample.

Based on the experimental measurement, average volume change at each point in time is plotted in FIG. 5.

In a sixth step 150, release of latent heat during solidification $q_s(t)$ is calculated for a plurality of, or all, points in time.

Thermal analysis of solidification processes is known from e.g. Diószegi, A. & Svensson, I.: *On the problems of thermal analysis of solidification*, Materials Science and Engineering A (Impact Factor: 2.41). December 2005; 413: 474-479. The used method also named Fourier Thermal Analyze method is based on the numerical solution of the heat conduction equation.

In the general case of temperature dependent properties, this equation reads $$\rho C_p \frac{\partial T}{\partial t} = \nabla (k \nabla T) + \dot{q}_{sol} \quad (1)$$

where $\dot{q}_{sol}$ is the volumetric heat source term. If k is assumed constant, equation (1) can be expressed as $$\frac{\partial T}{\partial t} = \alpha \nabla^2 T + \frac{\dot{q}_{sol}}{C_v} \quad (2)$$

$$\alpha = \frac{k}{\rho C_p}$$

$$\rho C_p = C_v$$

Rearranging equation (2) and substituting $\dot{q}_{sol}$ by $q_s$ and $$\frac{\partial T}{\partial t}$$

by $\dot{T}$, the released heat rate in the solidification interval can be calculated as function of time t $$q_s = C_v \dot{T} - C_v \alpha \nabla^2 T \quad (3)$$

or $$q_s(t) = C_v(t)(\dot{T}(t) - Z_f(t)) \quad (4)$$

where $$Z_f(t) = \alpha(t) \nabla^2 T(t) \quad (5)$$

It should be noted that $Z_f(t)$ is termed the zero line since it coincides with the cooling curve when the source term is equal to zero, i.e. when the temperature is outside the solidification interval.

Integrating the released heat over the time interval of solidification, the latent heat of solidification can be expressed as $$L = \int_{t_b}^{t_e} q_s(t) dt \quad (6)$$

Considering the solidification interval, the released heat can then be used to express the evolution of fraction solid as a function of time, by a cumulative function, i.e.

$$f_s(t) = \frac{1}{L} \int_{t_b}^{t} q_s(t) dt \quad (7)$$

Considering equation (4), the volumetric heat capacity is unknown and can for the general case of one solidifying new phase be expressed as a linear combination of the values at the beginning and the end of the solidification interval, i.e.

$$C_V(t) = C_{V,b}[1 - f_s(t)] + C_{V,e} f_s(t) \quad (8)$$

Alloys used in industrial practice precipitate several phases during solidification. An example is the hypoeutectic cast iron where the solid phase at the beginning is primary austenite followed by the eutectic mixture of secondary austenite and graphite. For this particular case, the volumetric heat capacity is given by $$C_V(t) = C_V^{liq} f^{liq}(t) + C_V^{aus} f^{aus}(t) + C_V^{gr} f^{gr}(t) \quad (9)$$

$$f^{liq}(t) + f^{aus}(t) + f^{gr}(t) = 1 \quad (10)$$

$$f^{liq}(t) = 1 - f_s(t) \quad (11)$$

Volumetric heat capacity values for $C_{V,b}$, $C_{V,e}$, $C_V^{liq}$, $C_V^{aus}$ and $C_V^{gr}$ have to be calculated according to equation (2). Appropriate data can be calculated using models proposed in the literature to calculate heat capacity, $C_P$, and density of metals.

Considering equation (5), the thermal diffusivity $\alpha$ is unknown and can be expressed for the solidification interval by a similar linear combination as given for $C_V$, i.e.

$$\alpha(t) = \alpha_b[1 - f_s(t)] + \alpha_e f_s(t) \quad (12)$$

where the thermal diffusivity at the start and end of solidification, $\alpha_b$ and $\alpha_e$, can be found from equation (2) by considering the heat source $\dot{q}_{sol} = 0$, $$\alpha = \frac{\dot{T}}{\nabla^2 T} \quad (13)$$

Equations (4) and (5) include the cooling rate $\dot{T}$ and the Laplace operator $\nabla^2 T$. The cooling rate can be determined from the experimental measurement. The Laplace operator can be approximated by a simple finite difference approximation for the 1-D spherical case as shown in equation (14), involving the two measuring points.

$$\nabla^2 T = \frac{8(T_2 - T_1)}{R_2^2 - R_1^2} \quad (14)$$

where $T_1$ and $T_2$ are the measured central and surface temperature. $R_1$ and $R_2$ are the polar radial coordinates of the central and surface position where the temperature are registered. For the present case $R_1=0$ if the thermal field is concentric around the central thermocouple.

An iteration procedure for obtaining $q_s(t)$ (released heat during solidification) can now be established by considering equations (4), (5), (6), (7), (8) and (12) for the general case of one solidifying phase or considering the same equations but substituting equation (8) by a subroutine containing equations (9), (10) and (11) for the particular case of hypoeutectic cast iron.

Such an iteration procedure is solved by a robust numerical algorithm. A mathematical validation of the algorithm exists where the analyzed solidification data (cooling curves) were produced by a forward numerical solidification. The used heat release in the numerical simulation was recovered accurately by the iteration procedure.

Figure 6:
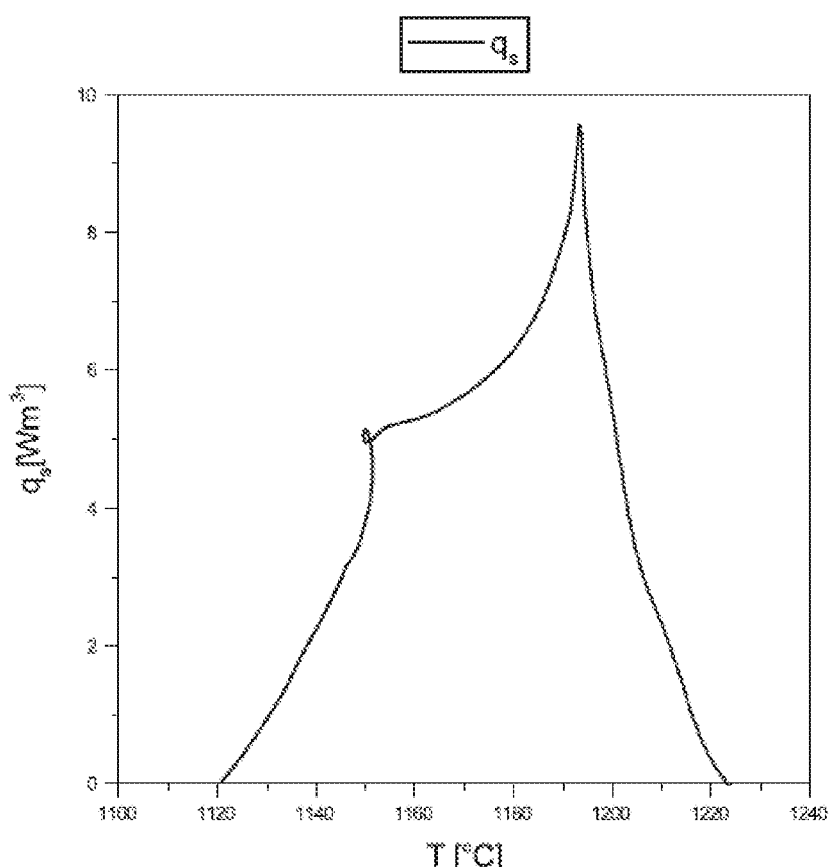
FIG. 6 shows calculated release of latent heat during solidification calculated by the Fourier Thermal Analyze method.

FIG. 6 is a diagram showing the released heat during solidification $q_s(t)$ as a function of temperature.

In a seventh step 150, the pressure in the inter granular liquid during solidification is calculated. A generally known formula from thermodynamics the Clapeyron equation (15) is used to calculate the pressure as a function of the local temperature, released latent heat and the volume change of the sample within the solidification interval.

$$\frac{dP}{dt} = \frac{\Delta H}{T * \Delta V} \quad (15)$$

If the pressure and the temperature vary along the phase transition line integration of equation (15) yield $$\left| \int_{P_1}^{P_2} dP = \frac{\Delta H}{\Delta V} \int_{T_1}^{T_2} \frac{1}{T} dT \right| \quad (16)$$

and obtain $$p_2 - p_1 = \frac{\Delta H}{\Delta V} \ln \frac{T_2}{T_1} \quad (17)$$

The outcome of the calculation $\Delta p$ is the pressure variation during solidification as a function of temperature and is obtained by inserting the calculated heat release during solidification and the measured volume change.

Figure 7:
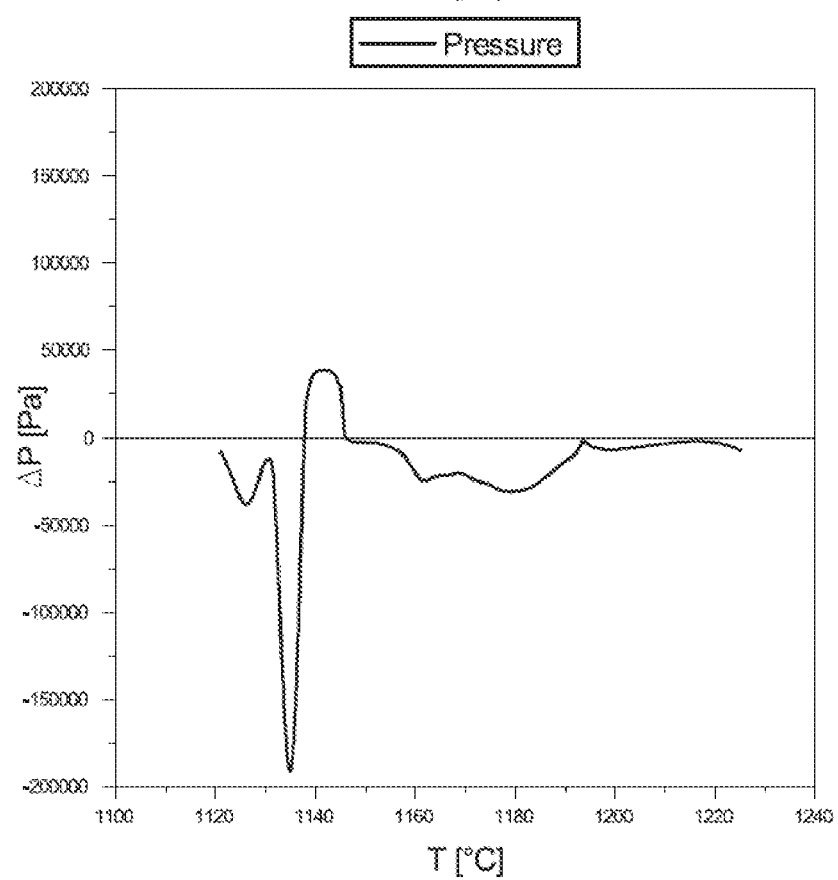
FIG. 7 shows calculated change in pressure in the solidification interval represented as a function of temperature.

FIG. 7 is a diagram showing the pressure during the solidification as a function of temperature.

The main outcome of the calculation representing the pressure state variation under solidification is shown in FIG. 7. The solidification starts with a slow variation and increase of depression until the minimum pressure is reached at 1185° C. where the primary crystal coherency is expected. A release of the depression continues and a positive pressure is accumulated within the temperature interval 1145 to 1135° C. corresponding the interval where the eutectic precipitation is dominated by graphite expansion. The last interval of the solidification develops once again a depression, deeper than during the primary austenite precipitation. The obtained solidification character can be interpreted as an alloy with a late depression which is not known from the literature and the max level of this negative spike can indicate the tendency for shrinkage porosity formation.

In order to be able to interpret the resulting pressure graphs, it will be necessary to perform tests, whereby samples are analyzed to provide pressure graphs according to the method disclosed above, and evaluated for defects, whereby defects are correlated to pressure graphs or parts of pressure graphs.

As mentioned by way of introduction, the disclosure is directed to a phase transformation from liquid to solid phase of a metallic material.

However, the method may be used for analyzing phase transformations from solid to solid in a material sample, e.g. a metal or metal alloy, which may transform between different solid phases.

The method may also be used to analyze phase transformations from solid to liquid, in which case the sample may need to be provided in a sample holder having sufficiently high melting point and the measurements may need to be provided in a temperature controlled, e.g. heated, environment.

In addition, the method may be used to analyze multiple phase transitions, such as liquid-solid-solid phase transformations.

Moreover, the method and/or the sampling device may be used to analyze phase transformations in polymeric material, including phase transformations taking place during the "solidification" or "melting" of a thermoplastic material (i.e. a thermoplastic polymer or a thermoplastic elastomer, e.g. around a glass transition temperature or a melting temperature), during the hardening of a thermosetting polymeric material, or during the cross-linking of a rubber or rubber-like polymeric material.

Moreover, the method may be used to analyze a hardening process of a concrete material.

Moreover, the method may be used to analyze the melting and/or solidification process of a glass material.

The material of the sampling device will be selected so as to be suitable for the material that is to be sampled.

Index
Capital Letters
$C_P$ Heat capacity, $Jkg^{-1}K^{-1}$
$C_P^{liq}$ Heat capacity of the liquid phase, $Jkg^{-1}K^{-1}$
$C_P^{aus}$ Heat capacity of the austenite, $Jkg^{-1}K^{-1}$
$C_P^{gr}$ Heat capacity of the graphite, $Jkg^{-1}K^{-1}$
$C_V$ Volumetric heat capacity, $Jm^{-3}K^{-1}$
$C_{V,b}$ Volumetric heat capacity at the start of solidification, $Jm^{-3}K^{-1}$
$C_{V,e}$ Volumetric heat capacity at the end of solidification, $Jm^{-3}K^{-1}$
$C_V^{liq}$ Volumetric heat capacity of the liquid phase, $Jm^{-3}K^{-1}$
$C_V^{aus}$ Volumetric heat capacity of the austenite, $Jm^{-3}K^{-1}$ $C_V^{gr}$ Volumetric heat capacity of the graphite, $Jm^{-3}K^{-1}$
L, $\Delta H$ Latent heat of solidification, $Jkg^{-1}$
$R_1$, $R_2$ Space position, m
$\dot{T}$ Cooling rate, $°Cs^{-1}$
T Temperature, $°C$
$T_1$ Temperature in central point, $°C$.
$T_2$ Temperature in lateral point, $°C$.
$T_{liq}$ Liquidus temperature, $°C$.
$T_{tr}$ Temperature at primary to eutectic transition, $°C$.
$T_{sol}$ Solidus temperature, $°C$.
$Z_F$ Fourier zero line, $°Cs^{-1}$
Small Letters
$f_s$ Fraction solidified metal
$f^{liq}$ Fraction liquid
$f^{aus}$ Fraction austenite
$f^{gr}$ Fraction graphite
$f_s^{tr}$ Fraction solidified at primary to eutectic transition
$f_{s\ sim}^{tr}$ Fraction solidified at primary to eutectic transition, input for simulation
$t_{s\ inv}^{tr}$ Fraction solidified at primary to eutectic transition, calculated by the inverse method
k, $k_i$ Thermal conductivity, $Wm^{-1}K^{-1}$
$\dot{q}_{sol}$, $q_s$ Released heat during solidification used in heat conduction equation, $Wm^{-3}$
$t_b$ Start time of solidification, s
$t_e$ End time of solidification, s
Greek Letters
$\alpha$ Thermal diffusivity, $m^2s^{-1}$
$\alpha_b$ Thermal diffusivity at the start of solidification, $m^2s^{-1}$
$\alpha_e$ Thermal diffusivity at the end of solidification, $m^2s^{-1}$
$\nabla^2 T$ Laplace operator
$\rho$ Density, $kgm^{-3}$
$\rho^{liq}$ Density of liquid, $kgm^{-3}$
$\rho^{aus}$ Density of austenite, $kgm^{-3}$
$\rho^{gr}$ Density of graphite, $kgm^{-3}$

The invention claimed is:

1. A method of analyzing a phase transformation of a material, comprising:
   providing a spherical sample of the material,
   measuring and recording a first data series of core temperature at the sample's center of gravity,
   measuring and recording a respective second data series of temperature at the sample's periphery,
   measuring and recording a respective third data series of radial displacements at the sample's periphery, and
   calculating a change in pressure in the sample at a plurality of points in time in based on said first, second and third data series, said change in pressure being caused by the phase transformation of the sample.

2. The method as claimed in claim 1, further comprising presenting the calculated change in pressure on a user interface.

3. The method as claimed in claim 1 or 2, wherein
   the peripheral temperature is measured in at least two spaced apart points on the periphery of the sample, and
   wherein the displacements are measured in at least two spaced apart points on the periphery of the sample, and said at least two points define a three-dimensional geometric body.

4. The method as claimed in claim 1, wherein at least one of the peripheral temperatures is measured in a point where also displacement is measured.

5. The method as claimed in claim 1, wherein the measuring steps are performed until the material has reached an end of the phase transformation process.

6. The method as claimed in claim 1, further comprising reducing noise in at least one of the data series.

7. The method as claimed in claim 1, further comprising calculating an average temperature of the sample's periphery and/or radial displacement over at least two points of said plurality of points in time.

8. The method as claimed in claim 1, wherein the phase transformation is selected from a group consisting of:
   a transformation from liquid phase to solid phase,
   a transformation from a first solid phase to a second, different solid phase, and
   a transformation from a solid phase to a liquid phase.

9. The method as claimed in claim 1, wherein the material is selected from a group consisting of:
   a metallic material or a metal alloy,
   a polymeric material,
   a concrete material, and
   a glass material.

10. The method as claimed in claim 1, wherein at least one of the temperature at the sample's periphery and the radial displacements at the sample's periphery is measured in at least four points, which define a three-dimensional geometric body.

11. The method as claimed in claim 10, wherein the four points where the temperature and/or the four points where the displacements are measured define a tetrahedron, preferably a regular tetrahedron.

12. The method as claimed in claim 1, further comprising calculating a release of latent heat ($q_s(t)$) at said plurality of points in time, during at least a phase transformation time interval, based on the first, second and third data series.

13. The method as claimed in claim 12, further comprising calculating the change of pressure in the sample at said plurality of points in time, based on the release of latent heat (qs(t)), the temperature at the sample's periphery and/or the temperature at the sample's center of gravity and a volume change, for the respective point in time.

14. A device for analyzing a phase transformation of a material, comprising:
   a gripping device for holding a spherical sample of the material,
   a first measuring device for measuring a first data series of core temperature at the sample's center of gravity,
   a second measuring device for measuring a respective second data series of temperature at the sample's periphery,
   a third measuring device for measuring a respective third data series of radial displacements at the sample's periphery, and
   a processing device, arranged to receive the first, second and third data series and for calculating a change in pressure in the sample at a plurality of points in time in based on the first, second and third said data series, said change in pressure being caused by the phase transformation of the sample.

15. The device as claimed in claim 14, further comprising a sample holder comprising a substantially spherical receptacle for holding the sample at least when the sample is in a liquid phase.

* * * * *